(12) United States Patent
Legen et al.

(10) Patent No.: US 8,753,681 B2
(45) Date of Patent: Jun. 17, 2014

(54) PHARMACEUTICAL COMPOSITION COMPRISING AT LEAST ONE ACTIVE AGENT AND A BINDER, WHICH SWELLS IN AN ACIDIC MEDIA

(75) Inventors: Igor Legen, Ljubljana (SI); Mateja Burjak, Ljubljana (SI)

(73) Assignee: LEK Pharmaceuticals D.D., Ljubljaa (SI)

( * ) Notice: Subject to any disclaimer, the term of this patent is extended or adjusted under 35 U.S.C. 154(b) by 32 days.

(21) Appl. No.: 12/746,335

(22) PCT Filed: Dec. 5, 2008

(86) PCT No.: PCT/EP2008/066889
§ 371 (c)(1),
(2), (4) Date: Jul. 30, 2010

(87) PCT Pub. No.: WO2009/074517
PCT Pub. Date: Jun. 18, 2009

(65) Prior Publication Data
US 2010/0297227 A1  Nov. 25, 2010

(30) Foreign Application Priority Data
Dec. 11, 2007  (EP) .................................. 07122877

(51) Int. Cl.
*A61K 9/20* (2006.01)
*A61K 9/28* (2006.01)
*A61K 31/22* (2006.01)

(52) U.S. Cl.
CPC ............. *A61K 9/2054* (2013.01); *A61K 9/2866* (2013.01); *A61K 31/22* (2013.01)

USPC .......................................................... 424/465

(58) Field of Classification Search
None
See application file for complete search history.

(56) References Cited

U.S. PATENT DOCUMENTS

| | | | |
|---|---|---|---|
| 6,669,955 B2 * | 12/2003 | Chungi et al. | 424/464 |
| 2003/0114497 A1 * | 6/2003 | Alani et al. | 514/355 |
| 2004/0247673 A1 | 12/2004 | Fergione et al. | |
| 2006/0204578 A1 * | 9/2006 | Vergez et al. | 424/473 |
| 2007/0014846 A1 * | 1/2007 | Holm et al. | 424/451 |
| 2007/0190138 A1 | 8/2007 | Holm | |
| 2011/0144181 A1 * | 6/2011 | Dyar et al. | 514/423 |

FOREIGN PATENT DOCUMENTS

| | | |
|---|---|---|
| EP | 0 284 849 | 10/1988 |
| EP | 0 812 589 | 12/1997 |

(Continued)

OTHER PUBLICATIONS

International Search Report for International Application No. PCT/EP2008/066889 mailed Apr. 8, 2009.
Agrawal et al. "Effect of Binders on Sulfamethoxazole Tablets." *J. of Pham. Sci.* vol. 77. No. 10. 1988. pp. 885-888.

(Continued)

*Primary Examiner* — Bethany Barham
(74) *Attorney, Agent, or Firm* — Merchant & Gould P.C.

(57) ABSTRACT

The invention relates to a pharmaceutical composition, which comprises at least one active agent and which further comprises a binder and/or a retarding agent, wherein the binder swells in an acidic medium, and the retarding agent retards the release of the active agent in an acidic or alkaline medium.

11 Claims, 1 Drawing Sheet

(56) References Cited

FOREIGN PATENT DOCUMENTS

| WO | WO 89/02266 | 3/1989 |
|---|---|---|
| WO | WO 92/00730 | 1/1992 |
| WO | WO 03/011283 | 2/2003 |
| WO | WO 2004/004778 | 1/2004 |
| WO | WO 2004/071403 | 8/2004 |
| WO | WO 2005/030183 | 4/2005 |
| WO | WO 2005/105036 | 11/2005 |
| WO | WO 2006/070248 | 7/2006 |

OTHER PUBLICATIONS

Lowenthal. "Mechanism of Action of Tablet Disintegrants." *Pharmaceutica ACTA Helvetiae* vol. 48. Nr. 11/12. 1973. pp. 589-609.

Sinha et al. "Binders for colon specific drug delivery: an invitro evaluation." *Int. J. of pharm.* vol. 249. 2002. pp. 23-31.

Yang et al. "Long-term Proton Pump Inhibitor Therapy and Risk of Hip Fracture." *JAMA* vol. 269. No. 24. 2006. pp. 2947-2953.

* cited by examiner

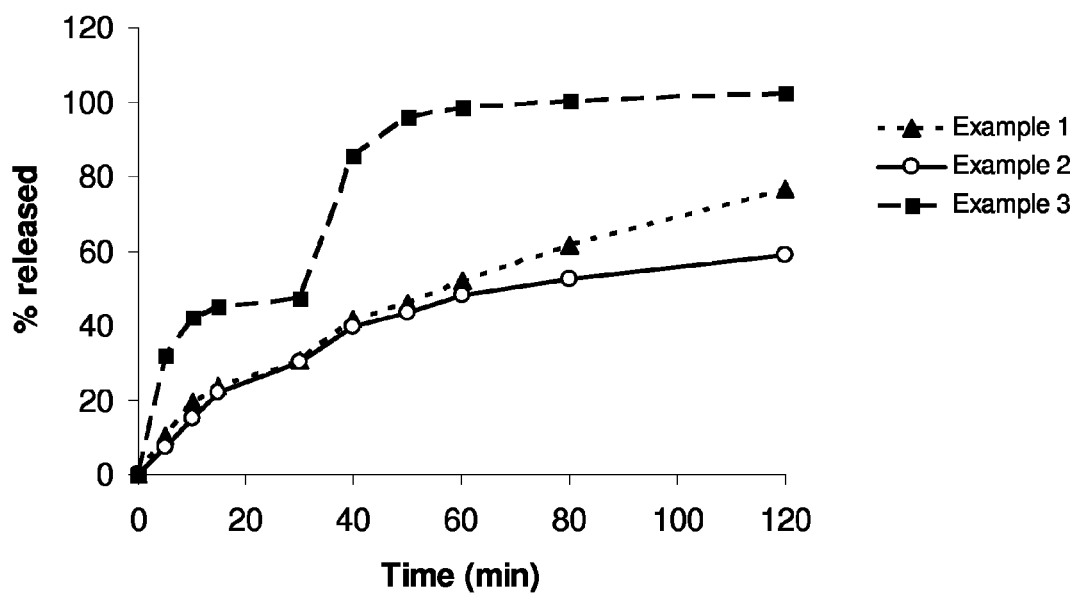

PHARMACEUTICAL COMPOSITION COMPRISING AT LEAST ONE ACTIVE AGENT AND A BINDER, WHICH SWELLS IN AN ACIDIC MEDIA

This application is a National Stage Application of PCT/EP2008/066889, filed Dec. 5, 2008, which claims benefit of Serial No. 07122877.9, filed Dec. 11, 2007 in the EPO and which applications are incorporated herein by reference. To the extent appropriate, a claim of priority is made to each of the above disclosed applications.

The present invention belongs to the field of pharmaceutical technology and relates to a pharmaceutical composition, which comprises at least one active agent and which further comprises a binder and/or a retarding agent, wherein the binder swells in an acidic media, and the retarding agent retards the release of the active agent in an acidic or alkaline medium.

Many pharmaceutically active agents exhibit pH-dependent dissolution and/or pH-dependent stability. For these active agents and compositions thereof the change of the gastric pH can significantly affect the release of the active agent from the composition, which results in altered pharmacokinetics and consequently in altered pharmacodynamics of the active agent. In case of an increased plasma concentration of an active agent the patient may experience enhanced side effects, while decreased plasma concentrations could result in the lack of the efficacy of the active agent. Active agents with decreased plasma concentrations, which are defined by the decreased peak plasma concentration ($C_{MAX}$) and/or area under the curve (AUC), due to an increase of the gastric pH and consequently impaired in vivo dissolution are for example poorly-water soluble weakly basic active agents. Specific examples of such active agents are the antifungal agent ketoconazole, the anti-emetic agent cinnarizine, the antibacterial agents enoxacin and cefpodoxime proxetil and the antianxiety agent diazepam. Additionally, calcium salts and zinc salts also exhibit impaired in vivo dissolution due to an elevated gastric pH.

On the other hand, the urinary antispasmodic agent tolterodine in its tartrate salt form is an example for an active agent with increased plasma concentrations, defined by an increased $C_{MAX}$, due to the concomitant use of a composition with a high amount of an alkalizing agent and, consequently, an increased in vivo dissolution of the active agent.

A further example of an active agent showing a pH dependency is atorvastatin. Atorvastatin is a weak acid with pKa=4.46, therefore its absorption from the gastrointestinal tract depends on the pH. At lower pH values atorvastatin is much better absorbed, because more of atorvastatin is in the un-ionised form, which can better pass the intestinal epithelium. Atorvastatin, and pharmaceutically acceptable salts thereof, are selective competitive inhibitors of HMG-CoA reductase. As such, atorvastatin calcium is a potent lipid lowering compound and is useful as a hypolipidemic and/or hypocholesterolemic agent. Atorvastatin is rapidly absorbed from the upper intestinal tract and reaches maximum plasma concentration after oral application in less than 2 hours. Atorvastatin exhibits its biological activity in the liver, and therefore high plasma concentrations of atorvastatin due to rapid absorption from the upper intestine are undesirable, because they may lead to extra-liver side effects including fatal rhabdomyolysis.

Hypercholesterolemia and hyperlipidemia are chronic conditions thus requiring chronic treatment. Both conditions frequently coexists with other diseases such as hypertension, diabetes, other heart and coronary diseases and other diseases. Therefore, frequent concomitant use of atorvastatin with other medications is expected. Other medications can be applied in the composition together with atorvastatin, such a composition is, e.g., a combination of atorvastatin with amlodipine, a medication used for the treatment of hypertension, or amlodipine can be applied in a separate composition.

In order to avoid high plasma concentration of atorvastatin marketed compositions, which comprise atorvastatin in combination with amlodipine, contain high amounts of alkalizing agents. The amount of alkalizing agent is high enough to increase the pH in the upper small intestine, which resulted in the decreased absorption from the upper small intestine and consequently in the lack of high plasma concentrations of atorvastatin.

Elevated gastric pH due to the administration of composition containing high amount of alkalizing agent may also afford the enhanced absorption of the acid-labile active agents, such as penicillins, erythromycin, used as antiinfectives, digoxin, used to treat congestive heart failure, or proton pump inhibitors.

Furthermore, an elevated gastric pH might also change the pharmacokinetic properties of the coated compositions (e.g. enteric coated ketoprofen tablets), because the pH in the stomach increase as a result of the concomitant use of composition with high amount of an alkalizing agent to the values that are characteristic for the small intestine. Thus, the release of the active agent may begin already in the stomach, resulting in an shorter $T_{MAX}$ (time to reach maximum concentration) and an increased $C_{MAX}$.

An additional problem, which may arise from the chronically increased pH in the stomach due to chronic application of compositions containing a significant amount of an alkalizing agent is the malabsorption of compounds which are essential for the normal body function and which require the acidic medium of the stomach for the dissolution and subsequent absorption. For example, it has been demonstrated that an increased pH in the stomach caused by long term treatment with proton pump inhibitors leads to the increased risk of hip fracture, as a result of calcium malabsorption, because an acidic environment in the stomach facilitates the release of ionized calcium from insoluble calcium salts (JAMA, 296, 2947-2954).

Therefore, in order to avoid the potential interactions between a composition comprising, e.g., atorvastatin and amlodipine, and concomitant medications a composition comprising atorvastatin and amlodipine without a significant amount of an alkalizing agent is specially encouraged.

Binders for pharmaceutical use are hydrophilic substances, such as sugars and polymers of natural and synthetic origin. The binders commonly used in pharmaceutical compositions are hydrophilic polymers, which because of their properties as film formers and viscosity builders are used in pharmaceutical compositions for a number of different purposes. Commonly used binders of natural origin include acacia, gelatin, starch, and hydrolyzed starch. They have been used widely in the past. In newer compositions they have been replaced by binders of synthetic origin, the most important of which are povidone and various cellulose derivatives. Binders are solid materials used in the manufacture of solid dosage forms because of their adhesive and cohesive properties. The role of binders is to assist size enlargement by adding cohesiveness to powders, thereby providing granules and tablets with the necessary bonding strength. Although binders improve the appearance, hardness and friability of these preparations, hitherto they are not intended to influence the disintegration or dissolution rates of the active substances.

Furthermore, in recent years, several newer disintegrants, often called "super disintegrants" have been developed. These kind of disintegrants (one of three classes of super disintegrants is modified cellulose=croscarmellose sodium) are not water soluble. Croscarmellose sodium is obtained by crosslinking carboxymethylcellulose sodium.

Compositions comprising atorvastatin and amlodipine containing high amount of an alkalizing agent are described in WO03/011283, where as high as 265.2 mg of $CaCO_3$ is present in the composition, and in WO2006/070248, where 25 mg of $Na_2CO_3$ is present in the composition. High amounts of an alkalizing agent in the composition comprising atorvastatin and amlodipine in a marketed composition (Caduet®) as described in WO 03/011283 and in the composition described in WO 2006/070248 can increase the gastric pH.

W. Lowenthal (Pharmaceutica Acta Helvetica, Vol. 48, Nr. 11/12 (1973) pp. 589-609), describes the use of carboxymethylcellulose as a disintegrant.

Agrawal Y K and Prakasam (K, J. of Pharmaceutical Sciences, Vol. 77, No. 10, (1998) pp. 885-889) describes the use of carboxymethylcellulose sodium as a binder in sulfamethoxazole tablets.

Sinha V R and Kumria, R (International Journal of Pharmaceutics, Vol. 249 (2002) pp 23-31) describes pharmaceutical compositions for site-specific active agent delivery in the colon using specific enteric coatings.

In contrast to the prior art, the inventors surprisingly found that instead of the use of alkalizing agents, it is possible to use specific binders in the production of a pharmaceutical composition to retard the release rate of an active agent. Especially, in order to develop an amlodipine-atorvastatin composition with a slow release of atorvastatin this new innovative approach was introduced. A pharmaceutical composition of the present invention includes an excipient which swells in acidic media resulting in a slow dissolution of atorvastatin. In addition, this excipient should dissolve at higher pH and release atorvastatin.

It was observed that pH dependent binders and/or retarding agents retard the release of the active agent, could be the ones with the desired properties.

Carboxymethylcellulose sodium, which is usually used as a film former, was introduced as an example for such a binder. Carboxymethylcellulose sodium swells in contact with water and forms an insoluble gel-like film with extremely low permeability to water. This could prevent the tablet disintegration and the release of the active substance. In addition, carboxymethylcellulose sodium gel becomes very viscous and the polymer chains cross-link through lactonization between carboxylic acid and free hydroxyl groups in the acidic gastric environment. Additionally, croscarmellose sodium may be used as a disintegrant. With the combination of carboxymethylcellulose sodium and croscarmellose sodium used in tablets, the desired slow release of atorvastatin from amlodipin-atorvastatin pharmaceutical composition may be obtained.

In order to retard the dissolution profile in the acidic and also in the alkaline medium, according to the present invention the above binder, e.g. carboxymethylcellulose sodium, may be partially or completely substituted with a retarding agent like hydroxypropyl methylcellulose (HPMC), which could be used as a dissolution rate controlling polymer. Furthermore, HPMC could be substituted with other retarding agents such as:

a) other cellulosic polymers like hydroxypropyl cellulose (HPC), hydroxyethylcellulose (HEC), methylcellulose (MC), ethylcellulose and cellulose acetate;

b) polyalkylene oxides, particularly poly(ethylene oxide), polyethylene glycol and poly(ethylene oxide)-poly(propylene oxide) copolymers;

c) acrylic acid and methacrylic acid polymers, copolymers and esters thereof, preferably formed from acrylic acid, methacrylic acid, methyl acrylate, ethyl acrylate, methyl methacrylate, ethyl methacrylate, and copolymers thereof, with each other or with additional acrylate species such as aminoethyl acrylate;

d) poly(olefinic alcohol) such as poly(vinyl alcohol); poly(N-vinyl lactams) such as poly(vinyl pyrrolidone), poly(N-vinyl caprolactam), and copolymers thereof;

e) polyvinylacetates, including polyvinylacetate per se as well as ethylene-vinyl acetate copolymers, polyvinyl acetate phthalate, and the like;

f) starch and starch-based polymers;

g) chitosan;

h) shellac, ammoniated shellac, shellac-acetyl alcohol, and shellac n-butyl stearate;

i) guar gum, xanthan gum, carageenan, alginates and pectin;

j) glyceryl monostearate and glyceryl behenate

Retarding agent is an agent that, when it is incorporated in the pharmaceutical composition, slow down the release of the active agent in acidic or alkaline medium HPMC and carboxymethylcellulose sodium used in the compositions of the Examples of the invention were of low viscosity grades:

HPMC: 12-18 mPas

Na CMC: 25-50 mPas

However, higher or lower viscosity grades polymers can also be used but with corresponding adjustment of polymer concentration: higher concentrations for lower viscosity grades and lower concentrations for higher viscosity grades.

Commercial grades of HPMC obtained from the market have good compression characteristics such that they can be directly compressed.

According to one preferred embodiment of the invention, high plasma concentrations of atorvastatin can be avoided by incorporating atorvastatin in a pharmaceutical composition comprising a binder, which swells in an acidic media and/or a retarding agent, which retards the release of the active agent in an acidic or alkaline medium, enabling slow dissolution of atorvastatin in the gastrointestinal tract and consequently slower absorption from the intestinal tract. In this connection slow dissolution of atorvastatin from the composition means that in 15 minutes between 10% and 30% of atorvastatin is released, in 30 minutes between 15% and 35%, in 60 minutes between 35% and 55% and in 120 minutes between 45% and 70% of atorvastatin is released from the composition.

In particular, according to the invention carboxymethylcellulose sodium is used as a preferred pH dependent binder which could prevent tablet disintegration and slows down the release of the active substance in the acidic gastric environment. As a preferred retarding agent, which retards the release of the active agent in an acidic or alkaline medium a retarding agent selected from the group consisting of hydroxypropyl methylcellulose, hydroxypropyl cellulose, hydroxyethylcellulose and methylcellulose is used.

However, beside pharmaceutical compositions comprising atorvastatin, the present inventive concept is also useful for other active agents that are rapidly absorbed from the upper small intestine, which are characterized in that the time to reach maximum plasma concentration (Tmax) is shorter than 2.5 hours, and which show undesired side effect(s) at high plasma concentrations, as a result of a rapid release in the stomach acidic medium. These active agents are for example other statins (e.g. fluvastatin, pravastatin), antimuscarinic agents (e.g. tolterodine) and other.

Furthermore, this inventive concept is also useful for active agents that damage the stomach and/or the small intestine due to high local stomach and intestinal concentrations that is reached as a result of a rapid release in the acidic medium. These active agents are for example non-steroidal anti-inflammatory active agents (e.g. ketoprofen, naproxen).

The pharmaceutical composition according to the invention is a composition which does not contain a significant amount of an alkalizing agent and shows a slow dissolution of the active agent in a physiologically relevant in vitro dissolution test.

In a preferred embodiment, the pharmaceutical composition comprises a combination of atorvastatin and another pharmaceutically active agent, characterized in that it is slowly absorbed from the gastrointestinal tract after oral application, which is represented by the time to reach maximum plasma concentration higher than 3 hours.

According to the invention, a pharmaceutical composition comprising at least one active agent and further comprises a binder and/or a retarding agent, wherein the active agent is an active agent which is rapidly absorbed from the upper small intestine such that the time to reach maximum plasma concentration (Tmax) is shorter than 2.5 hours, and that shows undesired side effect at high plasma concentrations or wherein the active agent is an active agent which damages the stomach and/or the small intestine due to high local stomach and/or intestinal concentrations is provided, which is characterized in that the binder swells in an acidic media and the retarding agent retards the release of the active agent in an acidic or alkaline medium.

The active agent which is rapidly absorbed from the upper small intestine may be selected from the group consisting of statins and antimuscarinic agents and is preferably atorvastatin.

In another preferred embodiment of the invention the active agent the active agent which damages the stomach and/or the small intestine due to high local stomach and/or intestinal concentrations is preferably selected from the group consisting of non-steroidal anti-inflammatory active agents.

In another preferred embodiment of the invention the pharmaceutical composition comprises a further pharmaceutical active agent, which is preferably slowly absorbed from the intestinal tract after oral application such that the time for reaching the maximum plasma concentration is more than 3 hours. As said further pharmaceutical active agent amlodipine or a pharmaceutically acceptable salt thereof is preferred.

In another preferred embodiment of the invention the pharmaceutical composition comprises said binder in concentrations 1-15% (w/w), preferably in concentrations 2-10% (w/w), more preferably in concentrations 2-8% (w/w). Preferably said binder is carboxymethylcellulose sodium.

In another preferred embodiment of the invention the pharmaceutical composition further comprises a retarding agent selected preferably from the group consisting of hydroxypropyl methylcellulose, hydroxypropyl cellulose, hydroxyethyl cellulose and methylcellulose. Retarding agents are added in concentrations 1-15% (w/w). Preferably in concentrations 2-10% (w/w). More preferably in concentrations 4-8% (w/w).

In another preferred embodiment of the invention the pharmaceutical composition further comprises a disintegrant. The disintegrant may be selected from the group consisting of croscarmellose sodium, crosslinked polyvinylpyrrolidone, crosslinked carboxymethyl starch, different types of starch and microcrystalline cellulose, magnesium aluminium silicate and any combinations thereof. Preferably the disintegrant is croscarmellose sodium. Disintegrants are added in concentrations 1-15% (w/w) to the total mass of the pharmaceutical composition. Preferably in concentrations 2-10% (w/w). More preferably in concentrations 2-8% (w/w).

In another preferred embodiment of the invention the pharmaceutical composition further comprises a filler. The filler may be selected from the group consisting of microcrystalline cellulose (MCC), modified forms of microcrystalline cellulose, lactose, sugars, different types of starch, modified forms of starch, and any combinations thereof. Fillers are added in concentrations 10-90% (w/w) to the total weight of the pharmaceutical composition. Preferably in concentrations 40-90% (w/w). More preferably in concentrations 60-80% (w/w).

In another preferred embodiment of the invention the pharmaceutical composition further comprises a lubricant/glidant. The lubricant/glidant may be selected from the group consisting of magnesium, calcium and zinc stearate, calcium behenate, sodium stearyl fumarate, talc, magnesium trisilicate, stearic acid, palmitic acid, carnauba wax, silicon dioxide and any combinations thereof. Lubricants and glidants are added in concentrations 0.1-10% (w/w) to the total mass of the pharmaceutical composition.

In another preferred embodiment of the invention the pharmaceutical composition further comprises an alkalizing agent. The alkalizing may be selected from the group consisting of organic or inorganic compounds which contain the groups having alkaline action and may be selected from the group consisting of:
a) oxides and hydroxides of alkaline and/or alkali-earth metals, oxides of the 4, 5 and/or 6 group of the periodic system such as MgO, MgOH, NaOH, $Ca(OH)_2$;
b) amines, such as trometamol (TRIS), ethanolamine, diethanolamine, triethanolamine, N-methyl-glucamine, glucosamine, ethylenediamine, diethylamine, triethylamine, isopropylamine, diisopropylamine;
c) alkali amino acids, such as arginine, histidine and lysine. Alkalizing agents are added in concentrations 0.1-10% (w/w) to the total weight of the pharmaceutical composition. Preferably in concentrations 0.5-5% (w/w).

Preferably the alkalizing agent is trometamol.

In another preferred embodiment of the invention the pharmaceutical composition further comprises a pharmaceutically acceptable additives, such as flavours, colorants, preservatives, sorbents and/or sweeteners.

In another preferred embodiment of the invention the pharmaceutical composition is coated. Preferred coating is described in WO 2004/071403. Preferably the coating comprises (a) a film-forming substance selected from the group consisting of polyvinyl alcohol, sodium carboxymelthylcellulose, hydroxyethylcellulose, and combinations thereof, (b) at least one pharmaceutical excipient selected from the group consisting of a buffering agent, an alkalizing agent and a surface active agent, and (c) optionally plasticizer.

In another embodiment present invention is related to a pharmaceutical composition comprising at least one active agent,
wherein the active agent is an active agent which is rapidly absorbed from the upper small intestine such that the time to reach maximum plasma concentration (Tmax) is shorter than 2.5 hours, and which shows undesired side effect at high plasma concentrations; or
wherein the active agent is an active agent which damages the stomach and/or the small intestine due to high local stomach and/or intestinal concentrations, characterized in that the composition further comprises a binder and/or a retarding agent, wherein the binder swells in an acidic media and the retarding agent retards the release of the active agent in an acidic or alkaline medium and wherein in 15 minutes between 10% and 30% of said active ingredient is released, in 30 minutes between 15% and 35% of said active ingredient is released, in 60 minutes between 35% and 55% of said active ingredient is released and in 120 minutes between 45% and 70% of said active ingredient is released from the composition.

In another embodiment present invention is related to a pharmaceutical composition comprising atorvastatin, or a pharmaceutically acceptable salt thereof, optionally in combination with further active agent, characterized in that the composition further comprises a binder and/or a retarding agent, wherein the binder swells in an acidic media and the retarding agent retards the release of the active agent in an acidic or alkaline medium and wherein in 15 minutes between 10% and 30% of atorvastatin is released, in 30 minutes between 15% and 35% of atorvastatin is released, in 60 minutes between 35% and 55% of atorvastatin is released and in 120 minutes between 45% and 70% of atorvastatin is released from the composition.

In another embodiment present invention is related to a pharmaceutical composition comprising at least one active agent, wherein the active agent is an active agent which is rapidly absorbed from the upper small intestine such that the time to reach maximum plasma concentration (Tmax) is shorter than 2.5 hours, and which shows undesired side effect at high plasma concentrations; or wherein the active agent is an active agent which damages the stomach and/or the small intestine due to high local stomach and/or intestinal concentrations, characterized in that the composition further comprises 1-15% (w/w) of binder and/or 1-15% (w/w) of a retarding agent, wherein the binder swells in an acidic media and retarding agent retards the release of the active agent in an acidic or alkaline medium In another embodiment present invention is related to a pharmaceutical composition comprising atorvastatin, or a pharmaceutically acceptable salt thereof, optionally in combination with further active agent, characterized in that the composition further comprises 1-15% (w/w) of binder and/or 1-15% (w/w) of a retarding agent, wherein the binder swells in an acidic media and retarding agent retards the release of the active agent in an acidic or alkaline medium In a particular preferred embodiment of the present invention, the pharmaceutical composition comprises atorvastatin, or a pharmaceutically acceptable salt thereof, in combination with amlodipine, or a pharmaceutically acceptable salt thereof, and carboxymethylcellulose sodium as a binder and hydroxypropyl methylcellulose as the retarding agent.

In another particular preferred embodiment of the present invention, the pharmaceutical composition comprises atorvastatin, or a pharmaceutically acceptable salt thereof, optionally in combination with amlodipine, or a pharmaceutically acceptable salt thereof, and
a) 1-15% (w/w) of carboxymethylcellulose sodium, and
b) 1-15% (w/w) of retarding agent, preferably hydroxypropyl methylcellulose.

In another particular preferred embodiment of the present invention, the pharmaceutical composition comprises atorvastatin, or a pharmaceutically acceptable salt thereof, optionally in combination with amlodipine, or a pharmaceutically acceptable salt thereof, and
a) 1-15% (w/w) of carboxymethylcellulose sodium,
b) 1-15% (w/w) of retarding agent, preferably hydroxypropyl methylcellulose, and
c) 1-15% (w/w) of disintegrant, preferably croscarmellose sodium.

In another particular preferred embodiment of the present invention, the pharmaceutical composition comprises atorvastatin, or a pharmaceutically acceptable salt thereof, optionally in combination with amlodipine, or a pharmaceutically acceptable salt thereof, and
a) 1-15% (w/w) of carboxymethylcellulose sodium,
b) 1-15% (w/w) of retarding agent, preferably hydroxypropyl methylcellulose,
c) 1-15% (w/w) of disintegrant, preferably croscarmellose sodium,
d) 10-90% (w/w) of filler,
e) 0.1-10% (w/w) of alkalizing agent, preferably trometamol, and
f) optionally a coating.

In another particular preferred embodiment of the present invention, the pharmaceutical composition comprises atorvastatin, or a pharmaceutically acceptable salt thereof, optionally in combination with amlodipine, or a pharmaceutically acceptable salt thereof, and
a) 2-10% (w/w) of carboxymethylcellulose sodium,
b) 2-10% (w/w) of retarding agent, preferably hydroxypropyl methylcellulose,
c) 2-10% (w/w) of disintegrant, preferably croscarmellose sodium,
d) 10-90% (w/w) of filler,
e) 0.5-5% (w/w) of alkalizing agent, preferably trometamol, and
f) optionally a coating.

In another particular preferred embodiment of the present invention, the pharmaceutical composition comprises atorvastatin, or a pharmaceutically acceptable salt thereof, optionally in combination with amlodipine, or a pharmaceutically acceptable salt thereof, and
a) 2-10% (w/w) of carboxymethylcellulose sodium,
b) 2-10% (w/w) of retarding agent, preferably hydroxypropyl methylcellulose,
c) 2-10% (w/w) of disintegrant, preferably croscarmellose sodium,
d) 40-90% (w/w) of filler,
e) 0.5-5% (w/w) of alkalizing agent, preferably trometamol, and
f) optionally a coating.

In another particular preferred embodiment of the present invention, the pharmaceutical composition comprises atorvastatin, or a pharmaceutically acceptable salt thereof, optionally in combination with amlodipine, or a pharmaceutically acceptable salt thereof, and
a) 2-8% (w/w) of carboxymethylcellulose sodium,
b) 4-8% (w/w) of retarding agent, preferably hydroxypropyl methylcellulose,
c) 2-8% (w/w) of disintegrant, preferably croscarmellose sodium,
d) 60-80% (w/w) of filler,
e) 0.5-5% (w/w) of alkalizing agent, preferably trometamol, and
f) optionally a coating.

The coating preferably comprises (a) carboxymethylcellulose sodium or hydroxyethyl cellulose or mixture thereof, (b) sodium laurilsulfate, (c) trometamol, and (d) glycerol.

Preferably the pharmaceutically acceptable salt of atorvastatin is atorvastatin calcium. Atorvastatin calcium may be in crystalline, non-crystalline or amorphous form, preferably in amorphous form.

FIGURE

FIG. 1 shows the dissolution of atorvastatin from slow (Example 1, Example 2) and fast (Comparative Example 3) dissolution compositions comprising atorvastatin and amlodipine.

The present invention is illustrated but in no way limited by the following examples:

EXAMPLES

Dissolution Properties

The dissolution properties of atorvastatin used as an active agent in the Examples were evaluated by a special in vivo relevant dissolution test, which is a combination of USP apparatus 1 (basket) and 2 (paddle). In this test a tablet is placed in a basket, the basket is fixed with a wire into the dissolution vessel in a way that the bottom of the basket was 5.5 cm above the bottom of the dissolution vessel and that the long axis of the basket is parallel with the long axis of the dissolution vessel and that the outer surface of the basket is in the contact with the dissolution vessel. The dimensions of the dissolution vessel, basket and the paddle are described in USP30, as well as the materials of which they are made of. 900 ml of artificial stomach juice (0.001 M HCl containing 45 mM $Na^+$, 9 mM $K^+$, 0.3 mM $Ca^{2+}$ and 54.6 mM $Cl^-$) is placed in the dissolution vessel, mixed with a paddle at 120 rpm and kept at 37° C. After 30 minutes (residence time of tablet in the stomach), 1.1 ml of saturated $NaHCO_3$ solution in water and 15 ml of saturated NaCl solution in water were added in the dissolution vessel in order to simulate transition of the tablet from the stomach to the small intestine. Samples were taken from the dissolution vessel at regular time intervals and the concentration of atorvastatin in the samples were analyzed by HPLC.

Preparation of Amlodipine-Atorvastatin Film Coated Tablets

Based on the use of micronized active substance, direct compression as the manufacturing process was used.

Mixture of silicified microcrystalline cellulose, atorvastatin, amlodipine, milled triturate of pigments and silicified microcrystalline cellulose and sieved trometamol and carboxymethylcellulose sodium (and Hydroxypropyl Methylcellulose—Example 2, or Pregelatinized Starch—Comparative Example 3) are homogenized and sieved. Sieved croscarmellose sodium (or Pregelatinized Starch—Comparative Example 3) is added and homogenized. In addition, sieved talc is added and homogenized. Finally, magnesium stearate is added and homogeneously mixed and compressed into tablets, mass 960 mg.

Polymer dispersion of carboxymethylcellulose sodium, hydroxyethyl cellulose, trometamol, sodium laurilsulfate, glycerol and water was prepared and coated in a perforated pan coating system. Film coated tablets are dried up to certain moisture content allowing stable pharmaceutical composition.

The composition of the film coated tablets used in the Examples 1, 2 and the (Comparative) Example 3 is shown in Table 1 below:

TABLE 1

Composition of Amlodipine-atorvastatin 10/80 mg film coated tablets

| Constituent | Example 1 | Example 2 | Example 3 (Comparative) | Function |
|---|---|---|---|---|
| Active: | | | | |
| Amlodipine besilate[1] | 13.870 mg | 13.870 mg | 13.870 mg | Active |
| Atorvastatin [1,2] | 80.000 mg | 80.000 mg | 80.000 mg | Active |
| Excipients core: | | | | |
| Silicified Microcrystalline Cellulose, dried[2] | 704.130 mg | 694.530 mg | 728.130 | Diluent |
| Carboxymethylcellulose Sodium | 81.600 mg | 28.800 mg | / | Binder |
| Hydroxypropyl Methylcellulose | / | 62.400 mg | / | Retarding agent |
| Pregelatinised Starch | / | / | 86.400 mg | Binder |
| Trometamol | 10.000 mg | 10.000 mg | 10.000 mg | Alkalizer |
| Ferric Oxide Black, E172 | 0.100 mg | 0.100 mg | 0.100 mg | Pigment |
| Ferric Oxide Red, E172 | 0.700 mg | 0.700 mg | 0.700 mg | Pigment |
| Magnesium Stearate | 2.400 mg | 2.400 mg | 2.400 mg | Lubricant |
| Talc | 9.600 mg | 9.600 mg | 9.600 mg | Glidant/lubricant |
| Croscarmellose sodium | 57.600 | 57.600 | / | Disintegrant |
| Pregelatinised Starch | / | / | 28.800 mg | Disintegrant |
| Weight of the tablet core: | 960.000 mg | 960.000 mg | 960.000 mg | |
| Excipients coating: | | | | |
| Carboxymethylcellulose Sodium | 44.903 mg | 44.903 mg | | Film former |
| Hydroxyethyl cellulose | 11.226 mg | 11.226 mg | 11.226 mg | Film former |
| Sodium Laurilsulfate | 1.571 mg | 1.571 mg | 1.571 mg | Solubilizer, surface active agent |

TABLE 1-continued

Composition of AmIodipine-atorvastatin 10/80 mg film coated tablets

| Constituent | Example 1 | Example 2 | Example 3 (Comparative) | Function |
|---|---|---|---|---|
| Trometamol | 4.509 mg | 4.509 mg | 4.509 mg | Alkalizer |
| Glycerol | 11.169 mg | 11.169 mg | 11.169 mg | Plasticizer |
| Total weight | 1033.378 mg | 1033.378 mg | 1033.378 mg | |

[1]Prior to manufacturing, the mass of pharmaceutically active agent is calculated according to the following equation:

$$X = \frac{Y \times 100\%}{Z\,(\%)}$$

X—pharmaceutically active agent per strength
Y—declared mass of pharmaceutically active agent (in mg per strength)
Z—assay of pharmaceutically active agent on the substance as it is (%)
[2]Atorvastatin is in the form of atorvastatin calcium The effect of the composition comprising atorvastatin and amlodipine on the gastric pH was evaluated by measuring the pH after dissolving the composition in 250 ml of 0.001 M HCl (represents the conditions in the stomach after the application of a glass of water). The results of this measurement are shown in Table 2:

TABLE 2

| Composition | pH |
|---|---|
| Simulated gastric media (no composition) | 3.02 |
| Example 1 | 5.27 |
| Caduet ® 10/80 | 7.66 |
| Caduet ® 10/40 | 7.63 |
| Caduet ® 10/20 | 7.59 |
| Caduet ® 10/10 | 6.83 |

As can be seen from Table 2, a pharmaceutical composition comprising atorvastatin and amlodipine prepared according to Example 1, shows only a modest increase of the pH of the simulated gastric media, while a much higher elevation in the pH was observed for the marketed composition comprising atorvastatin (10, 20, 40 and 80 mg) and amlodipine (10 mg).

As shown FIG. 1, a fast dissolution of atorvastatin from amlodipine-atorvastatin composition was obtained when pregelatinized starch which is partially soluble in water was used as binder/disintegrant (Example 3; Comparative Example). When this composition was subjected to bioequivalence study using 58 volunteers with the marketed composition (Caduet® 10/80), about 90% higher maximum plasma concentration (Cmax) of atorvastatin was observed for the composition prepared according Example 3 compared to the marketed composition.

Accordingly, fast dissolution of atorvastatin from amlodipine-atorvastatin composition was obtained when pregelatinized starch which is partially soluble in water was used as binder/disintegrant (Example 3; Comparative Example).

With the above concentration of carboxymethylcellulose sodium and croscarmellose sodium used in tablets of Example 1, the desired slow release of atorvastatin from amlodipin-atorvastatin pharmaceutical composition was obtained. When this composition was subjected to bioequivalence study using 53 volunteers with the marketed composition (Caduet® 10/80), only about 20% higher maximum plasma concentration (Cmax) of atorvastatin was observed compared to the marketed composition.

The invention claimed is:

1. A pharmaceutical composition comprising at least one active agent,
    wherein the active agent is an active agent which is rapidly absorbed from the upper small intestine such that the time to reach maximum plasma concentration (Tmax) is shorter than 2.5 hours, and which shows undesired side effect at high plasma concentrations; or
    wherein the active agent is an active agent which damages the stomach and/or the small intestine due to high local stomach and/or intestinal concentrations,
    wherein the composition further comprises:
    (a) from 2% to 8% of carboxymethylcellulose sodium as a binder;
    (b) from 2% to 8% of croscarmellose sodium as a disintegrant; and
    (c) optionally, from 4% to 8% of hydroxypropyl methylcellulose as a retarding agent
    and wherein the composition provides the following release profile:
    in 15 minutes between 10% and 30% of said active ingredient is released,
    in 30 minutes between 15% and 35% of said active ingredient is released,
    in 60 minutes between 35% and 55% of said active ingredient is released, and
    in 120 minutes between 45% and 70% of said active ingredient is released.

2. The pharmaceutical composition according to claim 1, wherein the active agent is selected from the group consisting of statins and antimuscarinic agents.

3. The pharmaceutical composition according to claim 2, wherein the active agent is atorvastatin or a pharmaceutically acceptable salt thereof.

4. The pharmaceutical composition according to claim 1, wherein the active agent is selected from the group consisting of non-steroidal anti-inflammatory active agents.

5. The pharmaceutical composition according to claim 1, wherein the composition comprises a further pharmaceutical active agent.

6. The pharmaceutical composition according to claim 5, wherein said further pharmaceutically active agent is slowly absorbed from the intestinal tract after oral application such that the time for reaching the maximum plasma concentration is more than 3 hours.

7. The pharmaceutical composition according to claim 5, wherein said further pharmaceutical active agent is amlodipine or a pharmaceutically acceptable salt thereof.

8. A pharmaceutical composition comprising atorvastatin, or a pharmaceutically acceptable salt thereof, and
  a) 2-10% (w/w) of carboxymethylcellulose sodium,
  b) 2-10% (w/w) of retarding agent,
  c) 2-10% (w/w) of disintegrant,
  d) 40-90% (w/w) of filler,
  e) 0.5-5% (w/w) of alkalizing agent, and
  f) optionally a coating.

9. A pharmaceutical composition according to claim 8 comprising atorvastatin, or a pharmaceutically acceptable salt thereof, in combination with amlodipine, or a pharmaceutically acceptable salt thereof, and
  a) 2-10% (w/w) of carboxymethylcellulose sodium,
  b) 2-10% (w/w) of retarding agent,
  c) 2-10% (w/w) of disintegrant,
  d) 40-90% (w/w) of filler,
  e) 0.5-5% (w/w) of alkalizing agent, and
  f) optionally a coating.

10. A pharmaceutical composition according to claim 8 comprising atorvastatin, or a pharmaceutically acceptable salt thereof, in combination with amlodipine, or a pharmaceutically acceptable salt thereof, and
  a) 2-10% (w/w) of carboxymethylcellulose sodium,
  b) 2-10% (w/w) of hydroxypropyl methylcellulose,
  c) 2-10% (w/w) of croscarmellose sodium,
  d) 40-90% (w/w) of filler,
  e) 0.5-5% (w/w) of trometamol, and
  f) optionally a coating.

11. The pharmaceutical composition according to claim 3 wherein said pharmaceutically acceptable salt of atorvastatin is amorphous atorvastatin calcium.

* * * * *